United States Patent [19]

Chan et al.

[11] Patent Number: 4,722,769
[45] Date of Patent: Feb. 2, 1988

[54] PROCESS FOR RECOVERY OF ACETONE

[75] Inventors: Chong H. Chan; Lamberto Crescentini; Everett H. Hinton, Jr., all of Chester, Va.

[73] Assignee: Allied Corporation, Morris Township, Morris County, N.J.

[21] Appl. No.: 855,232

[22] Filed: Apr. 24, 1986

[51] Int. Cl.$^4$ .......................... B01D 3/34; B01D 3/42
[52] U.S. Cl. ........................................ 203/30; 203/37; 203/94; 203/98; 203/99; 203/DIG. 6; 203/DIG. 18; 203/DIG. 19; 568/411
[58] Field of Search .................... 203/17, 36, 37, 91, 203/99, 2, DIG. 19, 30, 94, 98, DIG. 6, DIG. 18, 14, 28, 29; 202/205, 160; 568/411, 410

[56] References Cited

U.S. PATENT DOCUMENTS

| | | | |
|---|---|---|---|
| 2,737,480 | 3/1956 | Adams et al. | 568/411 |
| 2,906,675 | 9/1959 | Hall et al. | 568/411 |
| 3,668,256 | 6/1972 | Brundege | 568/411 |
| 3,672,961 | 6/1972 | Nixon, Jr. | 203/37 |
| 4,340,447 | 7/1982 | Laverick et al. | 203/37 |

FOREIGN PATENT DOCUMENTS

| | | | |
|---|---|---|---|
| 0747213 | 8/1970 | Belgium | 568/411 |
| 1191798 | 4/1965 | Fed. Rep. of Germany | 203/37 |
| 0571661 | 9/1945 | United Kingdom | 568/411 |
| 0640581 | 7/1950 | United Kingdom | 568/411 |
| 0753572 | 7/1956 | United Kingdom | 568/411 |
| 0817149 | 7/1959 | United Kingdom | 568/411 |
| 1060742 | 3/1967 | United Kingdom | 568/411 |
| 1195047 | 6/1970 | United Kingdom | 203/37 |
| 0570371 | 8/1977 | U.S.S.R. | 203/DIG. 19 |

Primary Examiner—S. Leon Bashore
Assistant Examiner—V. Manoharan
Attorney, Agent, or Firm—William H. Thrower

[57] ABSTRACT

This invention is a process for purifying crude acetone obtained by cleavage of cumene hydroperoxide, said crude acetone containing aldehyde impurities and appreciable amounts of unreacted cumene, by fractionally distilling the acetone in a multiple plate distillation column, said process comprising: continuously feeding crude acetone; continuously feeding a dilute aqueous solution of an alkaline material at a point above the crude acetone feed point; and controlling the temperature profile of the column by adjusting the amount of liquid acetone removed in step (c) to maintain a preselected temperature on a plate in the region between the crude acetone feed point and the alkaline material feed point.

12 Claims, 1 Drawing Figure

4,722,769

PROCESS FOR RECOVERY OF ACETONE

BACKGROUND OF THE INVENTION

1. Field of the Invention

The subject matter of the invention includes a process for recovery of pure acetone from the crude acetone containing aldehydic impurities and unreacted cumene which is obtained from the cleavage of cumene hydroperoxide.

2. Description of Related Art

An important process for production of phenol and acetone is the cumene hydroperoxide process wherein benzene is alkylated to cumene, which is oxidized to cumene hydroperoxide, which, in turn, is cleaved to produce phenol and acetone.

Varying amounts of side products such as aldehydes, particularly acetaldehyde and propionaldehyde, and other materials such as mesityl oxide, dimethylphenylcarbinol, alphamethylstyrene and acetophenone also result.

Phenol can be recovered by fractional distillation, with a crude acetone fraction removed from overhead. The crude acetone fraction contains those side products discussed above, as well as hydrocarbons such as unreacted cumene and alphamethylstyrene and traces of organic acids such as formic acid.

U.S. Pat. No. 4,430,447 to Laverick et al. describes a process for recovery of pure acetone from a crude acetone fraction which requires partial condensation of the crude acetone fraction, then feeding the resulting vapor phase only to a second distillation column for treatment with an alkaline material and distillation.

U.S. Pat. No. 3,668,256 to Brundege describes a process of fractionally distilling crude acetone in a single, multiplate column while continuously adding to the column aqueous alkali metal hydroxide at a specified ratio to reflux rate, in an amount and concentration sufficient to polymerize aldehyde impurities. Caustic strength is controlled by the ratio of reflux to caustic feed.

In practice, problems are encountered with the Brundege process if the crude acetone feed stream contains appreciable amounts of hydrocarbons, particularly unreacted cumene, which are not first removed from the crude acetone feed. It is desirable from a process and economic viewpoint to introduce substantially the entire crude acetone fraction, vapor and liquid, including any hydrocarbons and side-products that may be present. However, the cumene present in the crude acetone creates a cumene-rich oil phase which causes problems in operation of the column. The presence of an oil phase creates difficulty in caustic/aldehyde contact since the aldehydes are soluble in the oil phase and the caustic must then diffuse into the oil phase for contact. In practicing the Brundege process, the oil phase must be drawn off as a sidedraw from a plate or plates below the point of crude acetone feed. The inevitable result of the sidedraw of the oil phase is that economically significant amounts of the liquid phase containing caustic and acetone is drawn off also which must be separated from the oil and recycled with the caustic feed. This, however, creates further problems by introducing aldol condensation products, for example diacetone alcohol and further degradation products such as mesityl oxide, into the caustic feed, which can contact the acetone and increase the chance of acetone quality upsets.

The need exists for an efficient, economical process for the recovery of acetone from cumene-containing crude acetone.

SUMMARY OF THE INVENTION

Crude acetone containing water, cumene, and aldehydic impurities is fed to an intermediate point in a multiple-plate distillation column. A dilute aqueous alkaline solution is continuously fed at a point above the crude acetone feedpoint. The temperature profile of the column is controlled by adjusting product drawoff to maintain a preselected temperature on a tray in the region between the caustic and the crude acetone feed points. The oil, water and aldol condensation products discharge from the bottom and flow to oil/water separation facilities for recovery of cumene. Purified acetone substantially free from moisture and passing the standard potassium permanganate test is withdrawn from near the top of the column. Overhead vapors are condensed and returned as reflux. If necessary, a portion of the condensate can be returned to a point in the column between the crude acetone feed point and the alkali feed point to permit further contact of aldehydic impurities with caustic.

DESCRIPTION OF THE PREFERRED EMBODIMENT

Figure 1:
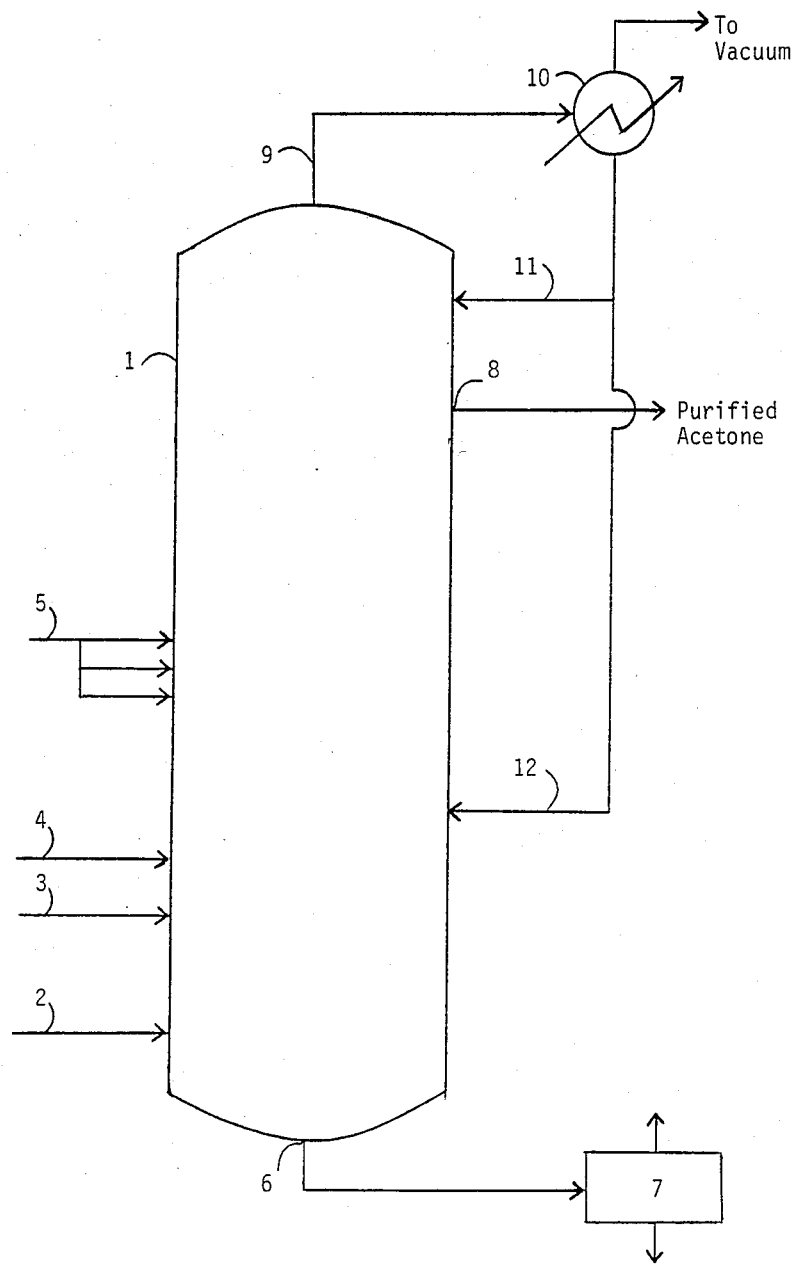
FIG. 1 shows a preferred arrangement of equipment useful in performance of the process.

Crude acetone containing water, cumene and aldehydic impurities can be purified to an extent wherein it will pass the standard potassium permanganate test, by combination of chemical treatment and distillation effected in a single, multiple-plate distillation column.

With reference to the Figure which shows a preferred arrangement of equipment useful in performance of the process, Column 1 is a single distillation column containing 60 plates or trays operating under reduced pressure. Heat source 2 supplies heat, for example in the form of steam to the bottom of the column.

Crude acetone containing water, unreacted cumene, and aldehydic impurities is continuously fed through vapor feed 3 at the sixth tray and liquid feed 4 at the seventh tray in any ratio of vapor to liquid. A dilute aqueous solution of alkali is continuously fed through feed inlet 5 at the nineteenth tray with alternate feed locations provided at the seventeenth and fifteenth trays. The alkali solution mixes with the down flowing liquid in the column and serves to scrub the upflowing vapors. This removes aldehydes by promoting aldol condensation reactions to produce high-boiling aldol condensation products which settle in the bottom of the column with water, any unreacted cumene, and the spent alkali. The bottoms are removed through discharge outlet 6 to oil/water separation facilities 7 where cumene is recovered for the cumene hydroperoxide reaction process.

Purified acetone, essentially free of water, i.e. less than 0.5 percent water and able to pass the standard potassium permanganate test, is withdrawn from the column through outlet 8, preferably located 3 to 5 trays below the top. Overhead vapor is removed through pipe 9 to condenser 10 and returned as reflux through pipe 11.

A portion of the overhead reflux can be fed through pipe 12 to a point between the crude acetone feed and the caustic feed, for example the eighth or eleventh tray, to afford additional contact with the caustic solution to insure essential aldehyde removal from the product when necessary.

The alkaline agent used to polymerize the aldehydes may be an appropriate inorganic basic material including alkaline earth oxides, carbonates and hydroxides and alkali metal oxides, carbonates and hydroxides. A dilute aqueous solution of about 0.2 to 2.0, preferably 0.8 to 1.5 percent sodium or potassium hydroxide is an example of an appropriate caustic solution. The control process of this invention has resulted in a substantial reduction over past practice in the amount of caustic solution added to the column. It is necessary to add only 1 to 5 percent caustic solution on a volumetric ratio to crude acetone feed. This provides substantial savings in caustic and in energy requirements since substantially less water is added with the caustic to the column.

The process of the present invention offers important advantages when the crude acetone feed contains appreciable amounts of unreacted cumene. Experience has shown that amounts as low as about 0.5 weight percent cumene in the crude acetone feed has created substantial problems in the Brundege process discussed above necessitating a sidedraw to remove oil from the column. The process of the present invention has successfully produced purified acetone when the crude acetone feed has contained as much as 4 weight percent cumene and 10 weight percent water.

Essential to the success of the process of this invention is control of the temperature profile of the column. The presence of the cumene creates an oil phase in addition to the aqueous caustic phase in the region between the caustic feed point and the crude acetone feed point. It is in this region that essential aldehyde/caustic contact occurs. However, the presence of two liquid phases interferes with the efficiency of this contact, and it becomes important to control precisely the temperature profile in this region.

In a distillation process, where the distillate is the desired product it is conventional to control the column at a point near to the point that distillate is withdrawn from the column. In the instant process, the product draw-off of purified acetone is of course grossly ratioed to the feed rate of crude acetone. However, for precise control of the temperature profile of the column, the product draw-off is adjusted to maintain a constant preselected temperature on a tray or plate in the region between the caustic feed point and the crude acetone feed points. It will be understood that the preselected temperature is dependent on the pressure in the column at that tray, and thus the preselected pressure compensated temperature is an indication of the composition profile at that point. With the 60-tray column being utilized, it has been found that there is sensitive interaction between the water and acetone profiles around the tenth tray and the product draw-off rate. Steam input at 2 is ratioed to the vapor and liquid feeds, in accordance with the relative amounts of vapor and liquid flows. The product draw off at 8 is ratioed to the feed rates, with the ratio adjusted by the pressure compensated temperature on the tenth tray. In this manner, essentially only acetone is in the overhead, and the cumene can be forced to the bottom with water, spent caustic, and the aldol condensation products.

The process of the instant invention has resulted in the elimination of the oil sidedraw necessary in the previously discussed U.S. Pat. No. 3,668,256 process. This has contributed significantly to the simplification of control requirements necessary to maintain composition profiles within the column. Absence of the oil sidedraw has presented many advantages: equipment is not necessary to recover acetone withdrawn with the oil sidedraw, lower caustic feed rate reduces the amount of water inventory in the column and allows reduction in steam usage, and only fresh caustic free from aldol product contamination is introduced at 5, thereby lessening the chance of acetone quality upsets. The process has resulted in increased acetone recovery combined with lower steam and caustic requirements, thus providing substantial savings in energy and materials.

EXAMPLE

Crude acetone containing impurities such as 500 ppm aldehydes, about 2 percent by weight cumene and about 10 percent by weight water was continuously fed to a 8 foot (2.44 meters) diameter 60 plate column. The overhead pressure was 360 mm Hg (48 kPa). The crude acetone was fed as a liquid to the seventh tray at a rate of 263 gallons per hour (994 liters per hour) and as a vapor to the sixth tray at a rate of 4602 liquid equivalent gallons per hour (17400 liters per hour). Steam was passed into the bottom of the column at a rate of 10,215 pounds per hour (4634 kgm per hour).

An aqueous 1 percent solution of sodium hydroxide was continuously fed to the nineteenth tray at a rate of 50 gallons per hour (189 liters per hour) and the distillation was carried out continuously, with the overhead vapors being removed, condensed, and a portion of the condensate returned to the top of the column as reflux, with the remaining portion of condensate fed to the eleventh tray at a rate of 128 gallons per hour (484 liters per hour).

Purified acetone product was withdrawn from the fifty-fifth tray at a rate of 4005 gallons per hour (15140 liters per hour). The product draw-off was ratioed to the crude acetone feed rates, with the ratio adjusted by the pressure compensated temperature on the tenth tray. For the given overhead pressure, the temperature on the tenth tray was maintained at 55° C. The acetone product contained 0.36 weight percent water and had a permanganate rating of 3.7.

A residue fraction containing cumene, water, excess alkali, and aldol condensation products was withdrawn from the base of the column to oil/water separation facilities and the cumene recovered.

What is claimed is:

1. A process for purifying crude acetone obtained by cleavage of cumene hydroperoxide, said crude acetone containing water, aldehyde impurities and appreciable amounts of unreacted cumene, by fractionally distilling the acetone in a multiple plate distillation column, said process comprising:
    (a) continuously feeding crude acetone to an intermediate point of the column;
    (b) continuously feeding a dilute aqueous solution of an alkaline material at a point above the crude acetone feed point;
    (c) reacting said aldehyde impurities with said alkaline material to produce aldol condensation products;
    (d) continuously removing from the column liquid acetone containing less than 0.5 percent water;
    (e) adding heat to said column to maintain a temperature profile and controlling the temperature profile of the column by adjusting the amount of liquid acetone removed in step (d) to maintain a preselected pressure compensated temperature on a plate in the region between the crude acetone feed point and the alkaline material feed point; and (f) removing from the base of the column a residue fraction comprising cumene, water, and aldol condensation products.

2. The process of claim 1 wherein said crude acetone contains at least 0.5 percent by weight of unreacted cumene.

3. The process of claim 2 wherein the column is operated at a reduced pressure in the range of from 300 to 550 mm Hg at the top of the column.

4. The process of claim 3 wherein said dilute aqueous solution of an alkaline material is an aqueous alkali metal hydroxide at a concentration of from 0.2 to 2.0 percent by weight.

5. The process of claim 4 wherein said aqueous alkali metal hydroxide solution is added in an amount of 1 to 5 percent on a volumetric ratio to crude acetone feed.

6. The process of claim 1 wherein the liquid acetone in step (d) is removed as a liquid sidedraw fraction from a point in the column between the alkaline material feed point and the top of the column.

7. The process of claim 6 additionally comprising removing an acetone vapor fraction from the top of the column, condensing said acetone vapor fraction and returning at least a portion of said condensate to the column at a point above the liquid acetone sidedraw point as reflux.

8. The process of claim 7 wherein said crude acetone contains at least 0.5 percent by weight of cumene.

9. The process of claim 8 wherein the column is operated at a reduced pressure in the range of from 300 to 550 mm Hg at the top of the column.

10. The process of claim 9 wherein said dilute aqueous solution of an alkaline material is an aqueous alkali metal hydroxide at a concentration of from 0.2 to 2.0 percent by weight.

11. The process of claim 10 wherein a portion of said condensate is returned to the column at a point between the crude acetone feed point and the alkaline material feed point.

12. The process of claim 11 wherein said aqueous alkali metal hydroxide solution is added in an amount of 1 to 5 percent on a volumetric ratio to crude acetone feed.

* * * * *